United States Patent [19]
Elloy et al.

[11] Patent Number: 4,791,919
[45] Date of Patent: Dec. 20, 1988

[54] SURGICAL INSTRUMENTS

[75] Inventors: Martin A. Elloy, North Yorkshire; Robert Johnson, Merseyside, both of England

[73] Assignee: Chas F Thackray Limited, Leeds, England

[21] Appl. No.: 822,035

[22] Filed: Jan. 24, 1986

[30] Foreign Application Priority Data

Jan. 25, 1985 [GB] United Kingdom ............... 8501907

[51] Int. Cl.⁴ ............................................. A61F 5/04
[52] U.S. Cl. ........................ 128/92 VW; 128/92 YZ; 128/92 VJ; 623/20
[58] Field of Search .......... 128/92 YZ, 92 V, 92 VV, 128/92 VY, 92 VZ, 92 VJ, 92 YW, 92 VD, 317, 92 Y, 92 YY, 92 VW; 623/18, 20, 16, 23

[56] References Cited

U.S. PATENT DOCUMENTS

| | | | |
|---|---|---|---|
| 3,696,446 | 10/1972 | Bousquet et al. | 623/20 |
| 3,763,855 | 10/1973 | McAtee | 128/92 YY |
| 4,135,507 | 1/1979 | Harris | 128/92 YZ |
| 4,169,470 | 10/1979 | Ender et al. | 128/82 YZ |
| 4,242,758 | 1/1981 | Amis et al. | 128/92 V X |
| 4,378,607 | 4/1983 | Wadsworth | 623/20 |
| 4,457,301 | 2/1984 | Walker | 128/92 YZ |
| 4,467,801 | 8/1984 | Whiteside | 128/92 VW X |
| 4,474,177 | 10/1984 | Whiteside | 128/92 VW X |
| 4,487,203 | 12/1984 | Androphy | 128/92 VW X |
| 4,562,598 | 1/1986 | Kranz | 623/20 X |
| 4,567,885 | 2/1986 | Androphy | 128/92 VW X |
| 4,621,630 | 11/1986 | Kenna | 128/92 VD |
| 4,627,425 | 12/1986 | Reese | 128/92 VJ X |

FOREIGN PATENT DOCUMENTS

| | | | |
|---|---|---|---|
| 0010527 | 4/1980 | European Pat. Off. | 623/20 |
| 2728427 | 1/1979 | Fed. Rep. of Germany | 623/20 |
| 1166261 | 11/1958 | France | 128/92 V |
| 0762877 | 9/1980 | U.S.S.R. | 128/92 VD |

OTHER PUBLICATIONS

Arthroplasty of the Knee, Article by J. M. Sheehan, from Instr. Mech. Engrs., C217/74, 1974, pp. 80–83.
Whiteside Ortholoc TM Total Knee System, a Publication of Dow Corning Wright, Form No. L095-0201, 1984.

Primary Examiner—Richard J. Apley
Assistant Examiner—David J. Bender
Attorney, Agent, or Firm—Henry Sternberg; Bert J. Lewen

[57] ABSTRACT

Instruments for use in the surgical implanation of a knee prosthesis including a femoral alignment rod for insertion into the medulla of a femur through an access hole located between the femoral condyles. The rod is resiliently deformable so that once the rod is fully inserted within the medulla the portion of the rod located within the medulla contacts the inner walls of the bone defining the medulla and is thus caused to bend. The access hole through which the rod is inserted is sufficiently larger than the diameter of the rod so as to impose no physical constraint on the rod for allowing the portion of the rod which protrudes from the access hole to extend linearly along an axis the position of which is determined by points of contact within the medulla between the rod and the inner walls of the medulla. According to further embodiments, the invention includes an angle adaptor for slideably and rotatably accommodating the protruding end of the alignment rod, and a method of surgically implanting a femoral component of a knee prosthesis.

17 Claims, 11 Drawing Sheets

SURGICAL INSTRUMENTS

BACKGROUND OF THE INVENTION

The present invention relates to instruments for use in the implanation of a knee prosthesis.

When fully extended, a vertical axis drawn through the centre of the femoral head passes through the centre of the knee joint and along the tibial medulla. This vertical axis is referred to as the mechanical axis, and it is along this axis that load is transmitted.

However, the femoral medulla lies at an angle of 6° to 8°, typically 7°, to this mechanical axis.

It is important therefore when implanting a knee prosthesis to maintain a horizontally aligned bearing surface between the tibial and femoral components so that load is transmitted as in a natural joint.

Currently known methods of ensuring the correct positioning of the femoral and tibial components on the femur and tibia respectively involve the use of an external guide rod which is fixed to the outside of the leg prior to surgery, using the vertical axis passing through the centre of the hip as a visual guide. With such a method it is extremely difficult to cut bone sufficiently accurately from the natural joint so that the prosthetic component is a precise fit and, for instance, is flush with a natural bone at its edges.

SUMMARY OF THE INVENTION

According to the present invention there is provided a set of instruments for use in the surgical implantation of a knee prosthesis, including a femoral alignment rod one end of which is for insertion into the medulla of a femur through an access hole located between the femoral condyles, said end being sufficiently blunt and said rod being of sufficient flexibility that the rod will not penetrate the bone of the femur but rather will bend to travel within the medulla, said rod being however of sufficient resilience to maintain its linearity within the femur as far as possible, said rod being of sufficient length to extend at least beyond the lesser trochanter with the other end of said rod protruding exteriorly from between the femoral condyles, the set of instruments further including an angle adaptor having an elongate body portion and also having means to allow the adaptor to be slid over and rotated about the protruding alignment rod with the longitudinal axis of the body portion of the adaptor forming an acute angle with the longitudinal axis of the alignment rod, said angle adaptor also having means rigidly to fix said angle adaptor to the femur.

The access hole should be of greater diameter than the diameter of the alignment rod such that when the alignment rod is fully inserted, it does not contact bone about the access hole. Accordingly the rod takes up a position dictated by points of contact within the medulla between the rod and the inner walls of the bone defining the medulla. It has been surprisingly found that with a rod which is as described above and which extends beyond the lesser trochanter and in which no constraint is placed on its position at or near the point of entry into the bone, the rod will adopt a position which is a constant distance from the anterior cortex of the femur at a point just proximal to the patella facets of the femoral condyles. This distance is typically 13.55 mm, and varies only in the range 13 to 15 mm. This is the case regardless of the size of the patient and the condition of the patient's bones. This discovery is utilised in this invention to enable a cutting guide to be located about the protruding rod so that precisely the correct amount of bone can be removed from, in particular, the front of the joint in what is termed anterior resection so that the resected surface is absolutely flush with the anterior cortex of the femur, and so, when fitted, the femoral component follows the profile of a natural joint.

Referring again to the rod itself, the end inserted into the bone is, as mentioned above, blunt (for instance a flat end with a chamferred peripheral edge in order to provide no sharp edges) and as it is pushed into the medulla it tries to take the easiest possible path down the middle. The bone is however curved and the rod hits harder bone and deflects. The rod is pushed in as far as it will reasonably go and the hardness of the bone wall maintains the bend in the rod. In practice the set of instruments may include a plurality of such rods of varying lengths, the surgeon chosing a rod of appropriate length for a particular patient so that, when inserted fully into the bone an appropriate length of rod protrudes as mentioned above. Typically the rod will protrude an amount of about 4 inches although the actual length of protrusion is one of convenience to the surgeon rather than essential to the invention.

Typically the rod diameter is from 5 to 7 mm, preferably from 5.5 to 6.5 mm and in one embodiment is about 6 mm diameter. The rod may be made of stainless steel or of some other appropriate material, such as another metal or a reinforced plastics material.

When located in position within the bone the rod is bent laterally to follow the curve of the bone. However, from the front the rod is straight and defines an axis of the femur.

When in position the rod extends linearily, as mentioned above, at an angle of approximately 7° to the mechanical axis extending from the hip joint along the axis of the tibia. The purpose of the angle adaptor is to compensate for this approximately 7° deviation from the mechanical axis.

Preferably the longitudinal axis of the body portion of the angle adaptor forms an angle of between 82° and 84° to the longitudinal axis of the femoral alignment rod.

Thus, the angle adaptor, when slid over the protruding femoral alignment rod defines a plane which is at an angle of approximately 83° to the axis of the alignment rod, and so which is perpendicular to the mechanical axis.

The plane defined by the angle adaptor forms a basis for the preparation of the femur to receive the femoral component of the knee prosthesis and ensures that the femoral component, when fitted, presents an articulating surface which is perpendicular to the mechanical axis.

Preferably the femoral alignment rod is of a sufficient length to extend beyond the lesser trochanter of the femur whilst still protruding from the femoral condyles.

In order to aid insertion of the femoral rod into the femoral medulla, an alignment rod intoducer is preferably included in the set of instruments. This has a handle portion and means to releasably grip an end of the alignment rod so that the introducer can be used to insert and rotate the alignment rod within the medulla.

Preferably the set of instruments includes a first femoral saw guide for resecting anterior and posterior portions of the distal end of the femur, the saw guide including means to accommodate the body portion of the angle adaptor, a central slot for slidably accommodating the protruding femoral alignment rod, a pair of upper slots for guiding a saw to resect an anterior portion of the femur, and one or more pairs of lower slots for guiding a saw to resect a posterior portion of the femur.

Preferably, a number of different pairs of lower slots are provided, the surgeon choosing the correct pair of slots to suit the size of the particular femoral component to be implanted.

Thus, in use, the first femoral saw guide is placed over the end of the femoral alignment rod and engages the body portion of the angle adaptor. When the first femoral saw guide is in place, a saw is passed through the upper slots to resect the anterior portion of the femur, and through the lower slots to resect the posterior portion of the femur. The engagement of the saw guide over the angle adaptor ensures that the resections are carried out in the correct plane.

Preferably the set of instruments includes a second femoral saw guide for resecting an inferior portion of the distal end of the femur, the saw guide including means to accommodate the body portion of the angle adaptor, a central slot for slidably accommodating the protruding femoral alignment rod, and upper and lower pairs of slots for guiding a saw to resect an inferior portion of the femur.

Thus, in use, the second saw guide is placed over the femoral alignment rod and the saw guide engages the body portion of the angle adaptor. A saw is then placed through the upper and lower pairs of slots to resect the inferior portion of the femur. Again, the engagement of the guide with the angle adaptor ensures that the resection is carried out in this correct plane.

Having carried out the resection, a femoral template may be placed over the resected portion to ensure that the correct degree of resection has been carried out.

Preferably the set of instruments includes a tibial alignment rod for insertion into the medulla of the tibia through an access hole located in the proximal end of the tibia, the rod being of sufficient length so as, when fully inserted, to protrude from said end, and one or more cutting tools for cutting a recess into the tibia, said tool or tools being adapted to rotate about an axis which is parallel to but horizontally displaced from the longitudinal axis of the tibial alignment rod.

Preferably said tool or tools includes a mandrel having an eccentric bore for engaging the tibial alignment rod and having an outer cylindrical surface with a longitudinal axis parallel to but horizontally displaced from the axis of the tibial alignment rod, said tool or tools being aranged for rotation about the cylindrical surface of said mandrel.

Preferably said tool or tools comprise a reamer for cutting out a surface of revolution in the proximal end of the tibia, and a broach for cutting an axial socket in the tibia.

Thus, the present invention gives the advantage that conical recesses for accommodating a tibial component may be formed in the tibia, the recesses being centred about an axis which is located posteriorly of the alignment rod, which is necessary so that the axis of rotation of the knee prosthesis, when implanted, is located behind the natural axis of the tibial medulla, ie. behind the mechanical axis.

Preferably the tibial alignment rod is of a sufficient length so as to extend close to the ankle joint whilst still protruding from the proximal end of the tibia.

Preferably the set of instruments includes a tibial saw guide for cutting a tibial plateau on the proximal end of the tibia, the saw guide comprising means to slidably and rotatably accommodate the protruding tibial alignment rod, and a pair of slots to guide a saw to cut a complete tibial plateau on the proximal end of the tibia.

Preferably the slots in the tibial saw guide are adjustable in position relative to the tibial alignment rod so as to allow the guide to be rotated about the whole of the tibia.

Thus, having inserted the tibial alignment rod, the tibial saw guide is used to cut a tibial plateau into the end of the tibia, by inserting the saw guide over the end of the tibial alignment rod and inserting a saw within the slots in the saw guide and rotating the saw guide around the whole of the tibia.

Having cut a tibial plateau, a reamer is used to cut a surface of revolution on the tibial plateau, to accommodate the shape of the articulating portion of the tibial component.

Preferably the set of instruments includes a constraining member which is in the form of a bifurcated pin for insertion through the tibia to engage a portion of the mandrel of the reamer to prevent excess reaming of the tibia.

Then a broach is tapped into the top of the tibia, either by means of a separate hammer or by means of an integral hammer, and used to cut an axial socket for the stem of the tibial component, the broach preferably including a stop collar to limit the depth of the axial socket cut.

Preferably the instruments are used with a tibial component of a knee prosthesis which has an eccentric bore therein to accommodate the tibial alignment rod.

Thus having cut the correct axial socket for the tibial component, the tibial component is pushed into the axial socket over the end of the tibial alignment rod.

Preferably the set of instruments includes a tibial impactor for pushing the tibial component of a knee prosthesis home within the axial socket, the impactor having an eccentric bore therein to accommodate the tibial alignment rod.

Preferably the set of instruments includes a femoral pusher having means to push a femoral component of a knee prosthesis home onto the resected portion of the femur, said pushing means being inclined at an angle of between 82° to 84° to the longitudinal axis of the femoral alignment rod.

Preferably the instruments are used with a femoral component of a knee prosthesis having an opening in its bearing surface through which the femoral alignment rod may pass.

Thus, a single set of instruments is used to prepare the femur and tibia and also to insert the femoral and tibial components in their correct positions on the femur and tibia.

Embodiments of the present invention will now be described by way of example only with reference to the accompanying drawings in which:

DESCRIPTION OF THE PREFERRED EMBODIMENTS

Figure 1:
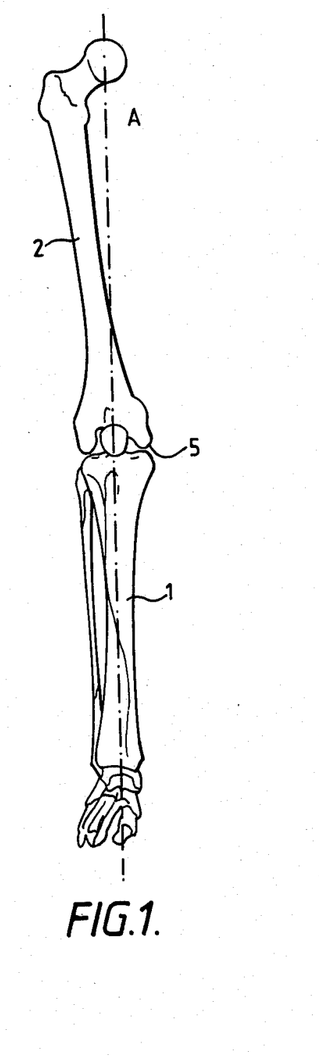
FIG. 1 is an anterior view of the femur and tibia.
Figure 2:
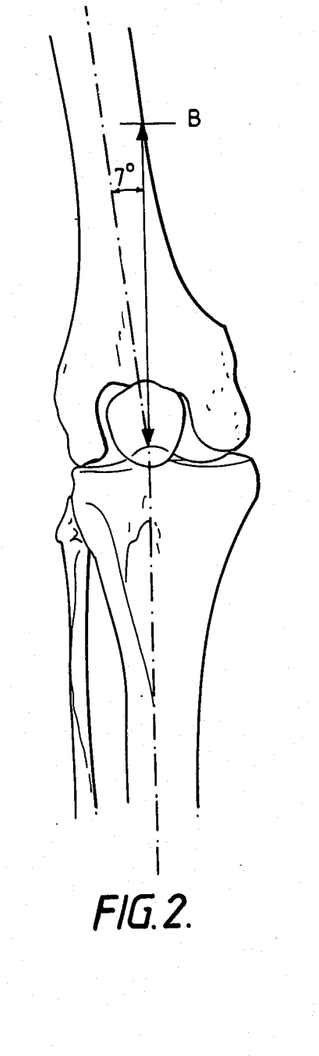
FIG. 2 is an enlargement of FIG. 1 showing the inclination of the axis of the femoral medulla to the mechanical axis.
Figure 2A:
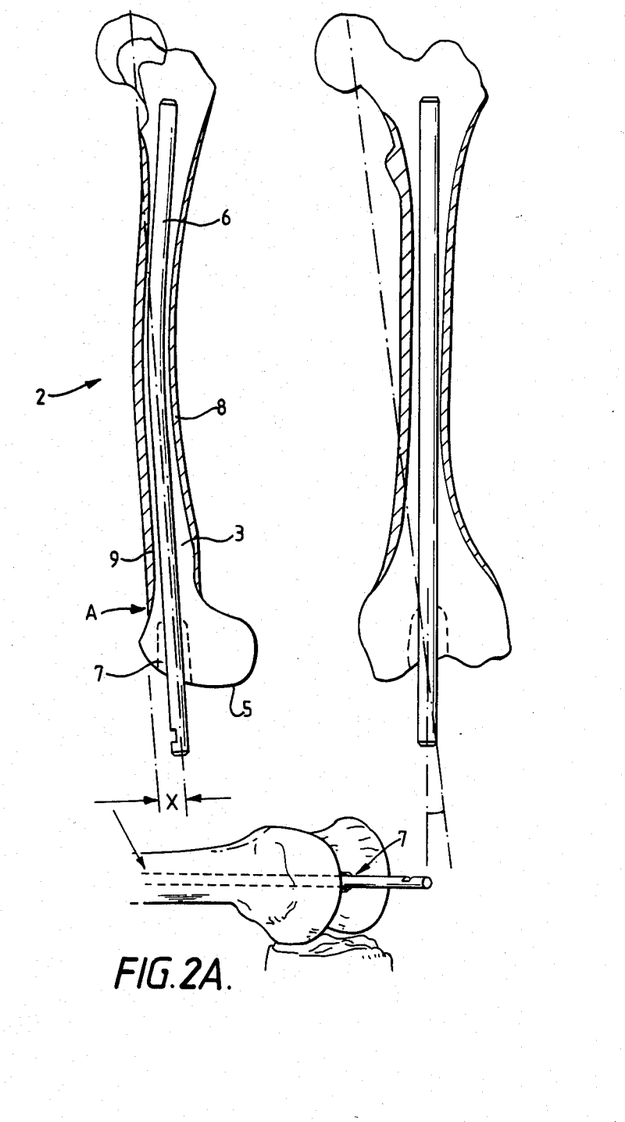
FIG. 2a shows both medio-lateral and anterior-posterior cross sections through the femur showing the position of the alignment rod.

The tibia 1 and femur 2 both include an elongate bore known as a medulla 3. The medulla 3 of the tibia 1 lies in a vertical axis, which, if extended, passes through the centre of the knee and through the head of the femur. The femur 2 has its medulla at an angle of approximately 7° to the vertical axis. However, the femoral condyles 5 are approximately parallel to a horizontal plane. An alignment rod 6, which may be of different length to accommodate different sizes of femur, for example 300 mm, 380 mm, 460 mm, is inserted through a large access hole 7 between the femoral condyle 5 and is pushed upwards into the femur to take up the position shown in FIG. 2a. The femoral alignment rod 6 makes contact with the posterior bone cortex 8 of the femur, which pushes the rod 6 forwards, and the rod is constrained anteriorly by the anterior bone cortex 9. This means that the rod 6 takes up a position which is offset by a distance X from the anterior surface of the femur in the region indicated by A, where X is typically 13.55mm, but may vary between 13 mm and 15 mm, and lies at an angle of approximately 7° to the vertical axis.

In order to easily move alignment rod 6 it is important to have an alignment rod introducer 10 which includes a handle 11 and a bore 12 for accommodating the alignment rod. Each alignment rod 6 includes a slot 6a near its end, i.e. an excavation within the confines of the profile of the rod, the rod being of intact integral unitary construction (cf. FIG. 3). The alignment rod introducer 10 includes a pivotal member 13 which is pivotted about point 13a to produce a rocking movement. At the end of member 13 is a projection 15 which may be accommodated in the slot 6a of the alignment rod. On the outer surface of alignment rod introducer 10 is a slidable sleeve 14 which slides readily along alignment rod introducer 10. The sliding of sleeve 14 bears against the rocking member 13 to cause the projection 15 either to be brought out of contact with the alignment rod or into contact with the alignment rod in slot 6a to fix the alignment rod introducer 10 to the end of the alignment rod 6. thus, with the help of handle 11, the alignment rod may be rotated, pulled or pushed into position, since slot 6a, as an excavation within the confines of the profile of alignment rod 6, accommodates the alignment rod introducer 10, serving as means releasably attachable or grippable thereat for thereby rotating, pulling or pushing the rod relative to the femur and its medulla.

Figure 3:
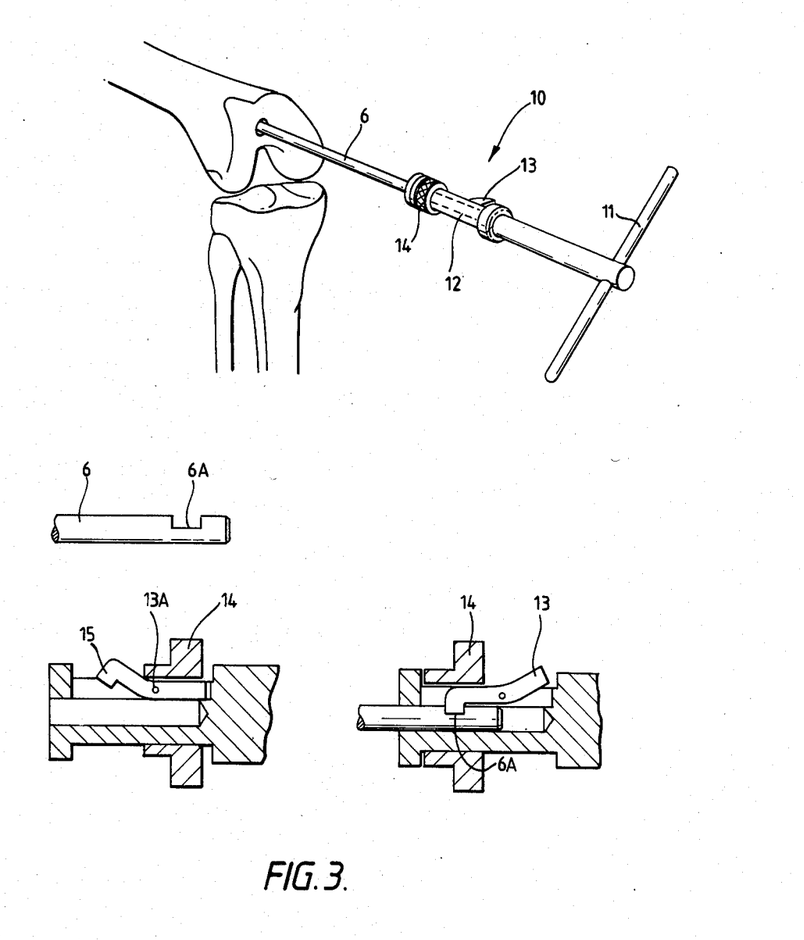
FIG. 3 is a perspective view of an alignment rod introducer being used to insert a femoral alignment rod.

In order to fit an alignment rod into the femur, a clearance hole 7 is first drilled into the intercondylar notch of the femur so that the alignment rod 6 may be aligned in the correct position within the femoral medulla 3. This then defines the angle of approximately 7° to the vertical axis. The alignment rod introducer 10 is then removed from the end of the alignment rod 6.

Figure 4:
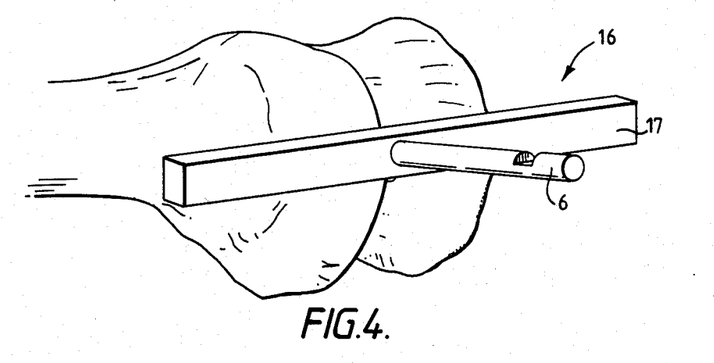
FIG. 4 shows the angle adaptor inserted over the femoral alignment rod.
Figure 4A:
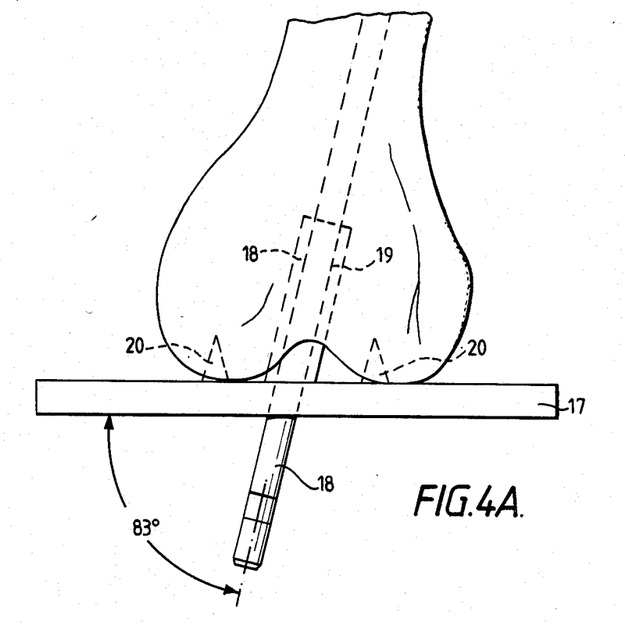
FIG. 4a is another view of the angle adaptor shown in FIG. 4, showing the mechanism for fixing the angle adaptor.

Referring now to FIGS. 4 and 4a, an angle adaptor 16 includes a bar 17 at an angle of approximately 83° to a tubular section 18 through which passes a bore 19 for accommodating the alignment rod 6. The angle adaptor 16 is inserted over the alignment rod 6 so that the bar 17 is parallel to the posterior condyles, as judged by the surgeon. The bar 17 includes on its inner surface two spikes 20 which key into the bone of the femur to fix the angle adaptor into the correct position.

Figures 5, 6:
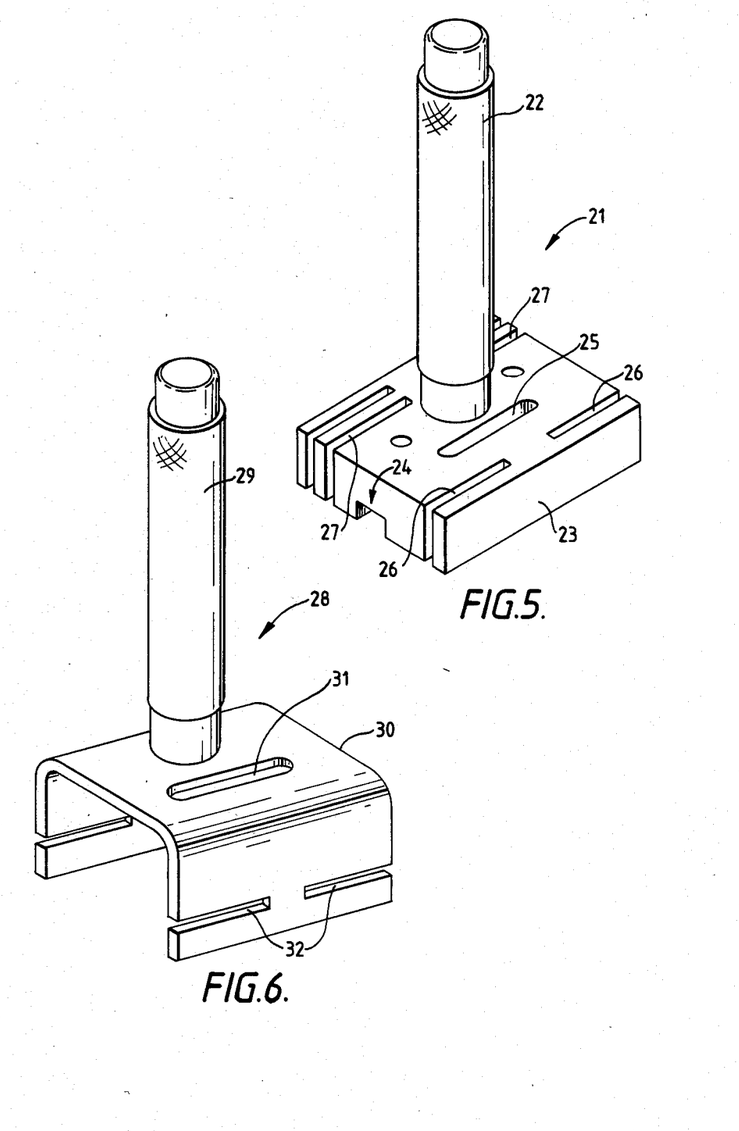
FIG. 5 is a perspective view of a first femoral saw guide.
FIG. 6 is a perspective view of a second femoral saw guide.
Figure 5A:
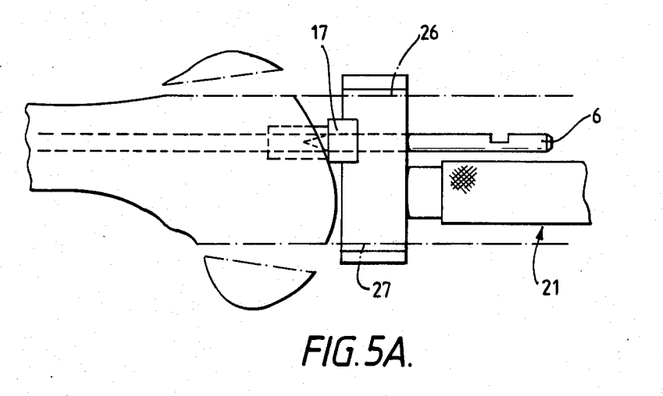
FIG. 5a shows the femoral saw guide shown in FIG. 5 being used to resect anterior and posterior portions of the femur.

Since the horisontal plane has now been located, saw guides may now be used to cut away the require shape for accommodating a femoral component of a knee prosthesis. A first femoral saw guide 21 includes a handle 22 and a perpendicular block 23. The block 23 includes a groove 24 for accommodating the bar 17 of the angle adaptor 16, and a slot 25 for accommodating the alignment rod 6. Upper saw guide slots 26 and lower saw guide slots 27 are parallel to the handle 22. The saw guide 21 is inserted over the angle adaptor 26 so that the groove 24 engages with the bar 17 of the angle adaptor 16, and the anterior resection of the femur is effected by inserting a saw through the upper saw guide slots 16. In a similar way, the posterior resection of the femur is carried out by inserting a saw in the lower saw guide slots 27 and in each case the cutting of the whole width of the femur is facilitated by sliding the saw guide 21 along the bar 17, whilst the alignment rod 6 slides along the slot 25.

Whilst the anterior resection is always carried out flush to the anterior surface of the femur, due to the constant distance of the alignment rod from the anterior cortex of the femur, the posterior resection depends on the size and type of the femoral component to be used. Therefore, although the upper slots 26 are always in the same position relative to the groove 24, there may be included a number of lower saw guide slots 27, the pair chosen to act as a saw guide depending on the type and size of the femoral component to be used.

Figure 6A:
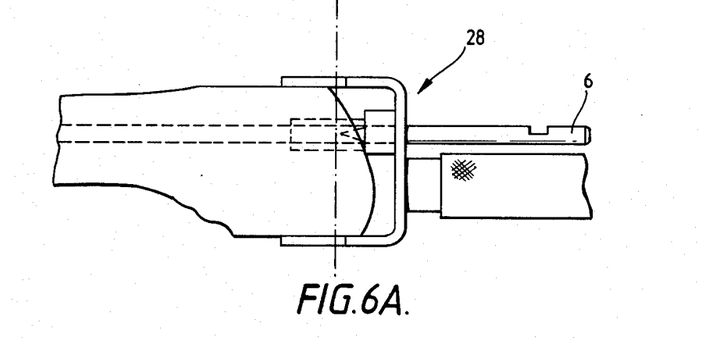
FIG. 6a shows the second femoral saw guide shown in FIG. 6 being used to resect an inferior portion of the femur.

Referring to FIG. 6, a second femoral saw guide 28 includes a handle 29 and a perpendicular block 30 which is in the form of a U-shaped channel. The width of the channel is the same width as the width between the two pairs of slots 26 and 27 on the first saw guide 21. Thus the second saw guide 28 may fit snuggly over the resected region of the femur. A slot 31 is used to accommodate the alignment rod, and slots 32 are perpendicular to the longitudinal axis of the handle 29 to allow the inferior resection of the femur, as shown in FIG. 6a. Again the saw guide 28 may be slid medially or laterally on the femur, since the alignment rod 6 slides along in the slot 31. A femoral template 33 such as that shown in FIG. 7 is used to check that the correct shape has been cut on the femur.

Figures 7, 8, 9:
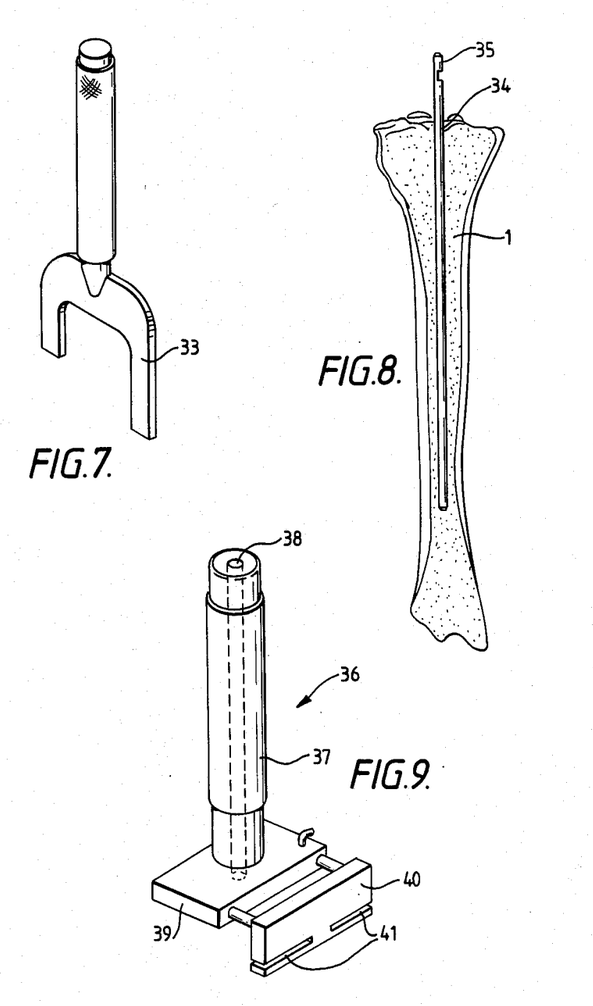
FIG. 7 shows a femoral template.
FIG. 8 shows a tibial alignment rod inserted within the tibia.
FIG. 9 is a perspective veiw of a tibial saw guide.

Referring now to FIG. 8, a hole 34 is drilled at the proximal end of the tibia 1, and a tibial alignment rod 35, identical to the femoral alignment rod 6, is introduced into the medulla of the tibia using alignment rod introducer 10. When the alignment rod 35 is in place within the tibia, the alignment rod introducer 10 is removed to leave the alignment rod 35 in position.

A horizontal plateau, known as the tibial plateau is then cut on the proximal end of the tibia, and this is achieved by using the tibial saw guide 36 shown in FIG. 9. The saw guide 36 includes handle 37 including a bore 38 for accommodating the alignment rod 35, and a fixed block 39 attached to the end of the handle. Slidably attached to fixed portion 39 is an extension piece 40 including two slots 41. The saw guide can then be used to cut a complete tibial plateau in the proximal end of the tibia, since the extension piece 40 can slide in and out of engagement with any obstruction on the outside of the tibia, as shown in FIG. 9a.

Figure 11:
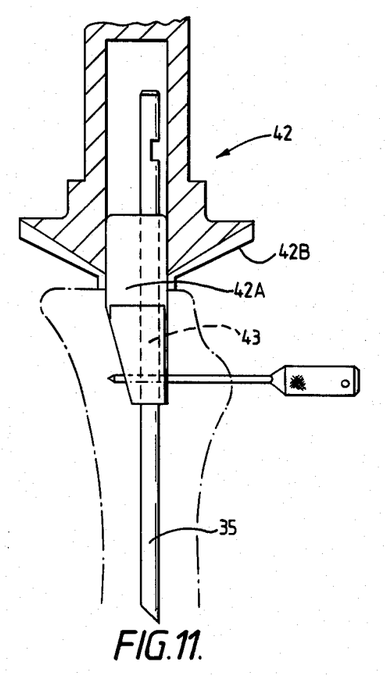
FIG. 11 shows a reamer for cutting a surface of revolution in the tibia, including a constraining pin.

Referring now to FIG. 11, a reamer 42 is used to cut a surface of revolution in the top of the tibial plateau. Each reamer 42 includes a mandral 42a with an eccentric bore 43 to accommodate the alignment rod 35 so as to produce a surface of revolution centred about the correct central axis. Each reamer has cutting edges 42b which cut into the tibia as the reamer is rotated.

Figures 9A, 10, 10A:
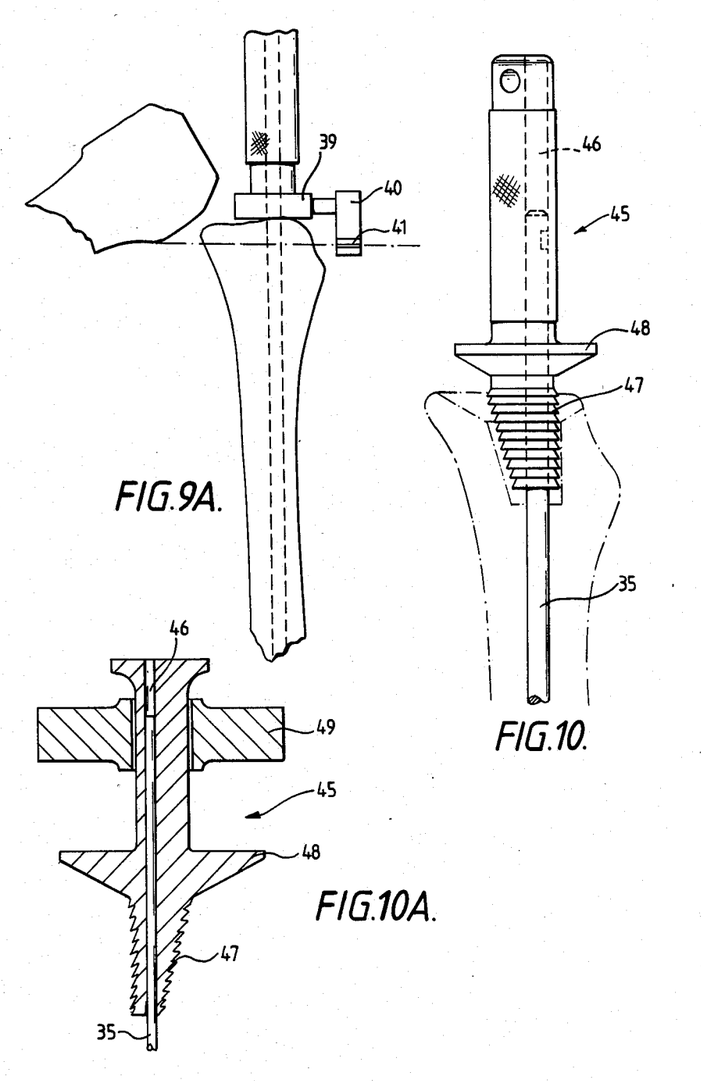
FIG. 9a shows the tibial saw guide shown in FIG. 9 being used to cut a tibial plateau on the tibia.
FIG. 10 shows a perspective view of a broach being used to cut an axial socket in the tibia.
FIG. 10a shows an alternative embodiment of a broach having an integral slide hammer.
Figure 10B:
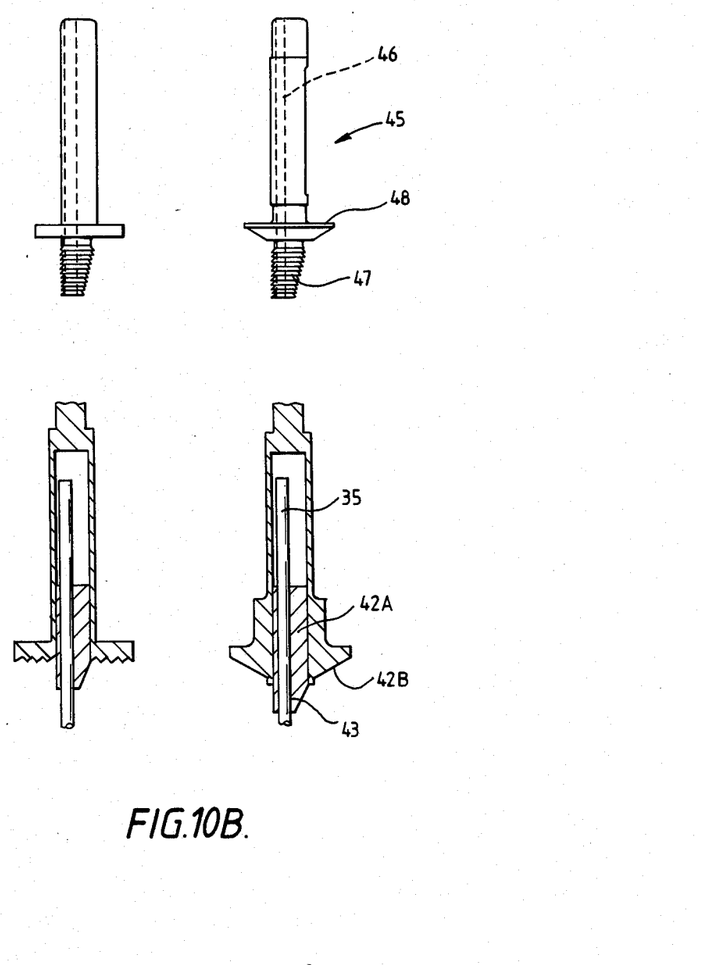
FIG. 10b shows examples of broaches and reamers.

Referring now to FIGS. 10, 10a and 10b, a broach 45 includes an eccentric bore 46 for accommodating the alignment rod 35, and a rasp section 47 for cutting the correct shaped axial socket in the tibial medulla. A suitably shaped collar section 48 prevents broaching to an excessive depth.

In the embodiments shown in FIG. 10, a separate hammer is used to impact the broach into the tibia, but in FIG. 10a an alternative embodiment is shown in which there is included an integral side hammer 49 to ensure that the force is applied in the correct place on the tibia.

The eccentricity of the bore 46 ensures that the axial socket is cut into the tibia about the correct central axis, which is horizontally displaced from the axis of the tibial alignment rod.

Figure 12:
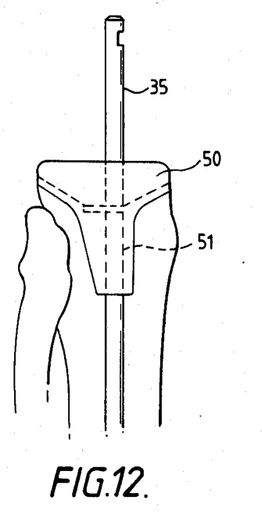
FIG. 12 shows a tibial component of a knee prosthesis inserted in place over the tibial alignment rod.
Figure 13:
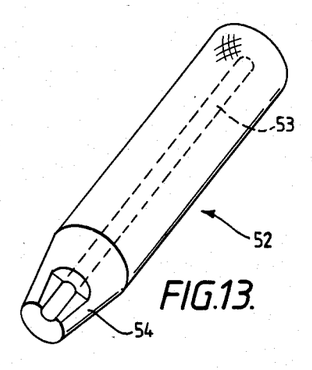
FIG. 13 is a perspective view of a tibial impactor.
Figures 14, 14A, 16, 16A:
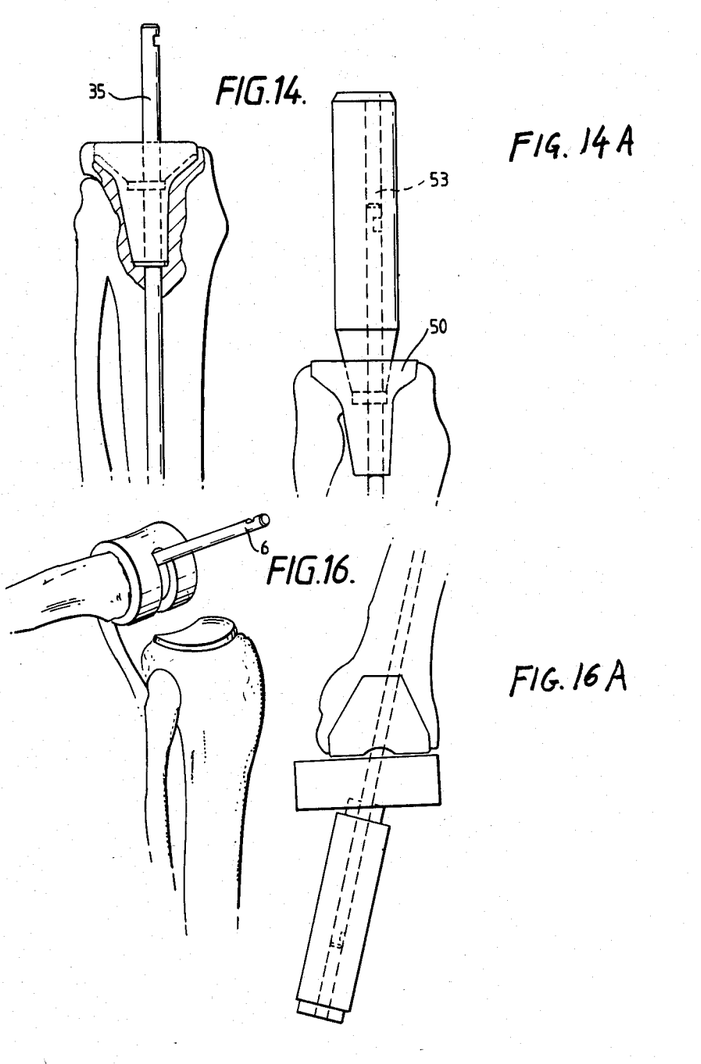
FIGS. 14 and 14a show the tibial impactor being used to push the tibial component home into the axial socket of the tibia.
FIGS. 16 and 16a show the femoral pusher being used to push the femoral component onto the resected end of the femur.

Once the axial socket has been cut, a tibial component 50 which includes an eccentric bore 51 for accommodating the alignment rod 35 is tapped home into the socket by means of a tibial impactor 52. The tibial impactor 52 includes an alignment rod bore 53 and a reduced diameter head 54 for engaging the articulating surface of the tibial component 50. This procedure is shown in FIG. 14.

Figure 15:
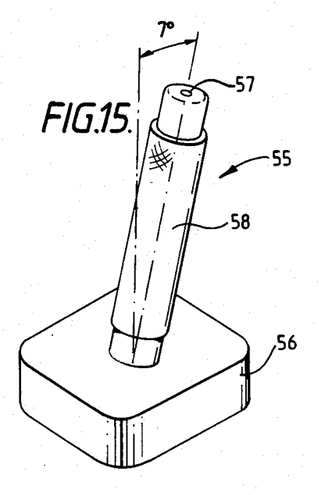
FIG. 15 is a perspective view of a femoral pusher.

The femoral component may then be introduced onto the femur using a femoral impactor 55. The head 56 of the impactor is at an angle of approximately 83° to the bore 57 within the handle 58 of the impactor. The femoral component includes an intercondylar gap which can accommodate the alignment rod as shown in FIG. 16, but in the case where a femoral component is used which does not have such a slot, preferably a hole is provided in the articulating surface to allow the alignment rod 6 to pass through. The impactor 55 is slid over the alignment rod 6, and used to push the femoral prosthesis into place. In the case of a three part knee, the third component of a knee prosthesis is then slipped into position between the tibial and femoral components.

Only at this point, when both components of the prosthesis have been inserted, are the alignment rods 6 and 35 removed from the femur and tibia respectively. The knee joint is then reassembled and the surgical operation completed.

Whilst the alignment rods 6 and 35 may be of any suitable metal, they are typically made of steel, and have a diameter of typically 6 mm.

It should be appreciated that the instruments of the present invention, whilst allowing the appropriate bone resections to be carried out in the correct planes, also provides a means for locating the femoral and tibial components into their respective correct positions, and this is particularly important when when bone cement is used, since in this case more bone is resected than is strictly necessary in order to leave a space for the bone cement, and without the alignment provided by the instruments of the present invention, accurate location of the components could not be achieved.

We claim:

1. A set of instruments for use in the surgical implantation of a knee prosthesis, the set including:
    a femoral alignment rod having a first blunt end for insertion within the medulla of a femur through an access hole located between the femoral condyles, and a second end opposite said first end, the length of the rod between said two ends being sufficient with respect to the particular femur undergoing surgery, and the rod being sufficiently flexible, to allow said second end to protrude from said access hole whilst said first end is located within the medulla at least beyond the lesser trochanter, the rod also being sufficiently resilient and the access hole being sufficiently larger than the diameter of the rod to impose no physical constraint thereon, such that once the rod is fully inserted within the medulla as aforesaid, the portion of the rod located within the medulla contacts the inner walls of the bone defining the medulla, whereby the portion of the rod which protrudes from the access hole is allowed to extend linearly along an axis the position of which is dictated by points of contact within the medulla between the rod and the inner walls of the medulla; and
    an angle adaptor comprising an elongate body portion having fixation means for rigidly fixing the adaptor to the femur, which elongate member includes means for slidably and rotatably accommodating the protruding end of the alignment rod with the alignment rod forming an acute angle in the medio-lateral plane with the body portion.

2. A set of instruments according to claim 1, in which the longitudinal axis of the body portion of the angle adapter forms an angle of between 82° and 84° to the longitudinal axis of the protruding part of the femoral alignment rod as measured in the medio-lateral plane.

3. A set of surgical instruments according to claim 1 and including a first femoral saw guide for resecting anterior and posterior portions of the distal end of the femur, the saw guide including means to accommodate the body portion of the angle adaptor, a central slot for slidably accommodating the protruding portion of the femoral alignment rod, a pair of upper slots for guiding a saw to resect an anterior portion of the femur, and one or more pairs of lower slots for guiding a saw to resect a posterior portion of the femur.

4. A set of instruments according to claim 1 and including a second femoral saw guide for resecting an inferior portion of the distal end of the femur, the saw guide including means to accommodate the body portion of the angle adaptor, a central slot for slidably accommodating the protruding portion of the femoral alignment rod, and upper and lower pairs of slots for guiding a saw to resect an inferior portion of the femur.

5. A set of instruments according to claim 1 and including a femoral pusher having means to push a femoral component of a knee prosthesis home onto the resected portion of the femur, said pushing means being inclined at an angle of between 82° to 84° to the longitudinal axis of the protruding portion of the femoral alignment rod.

6. A set of instruments according to claim 1 and including a tibial alignment rod for insertion into the medulla of the tibia through an access hole located in the proximal end of the tibia, the rod being of sufficient length so as, when fully inserted, to protrude from said end, and one or more cutting tools for cutting a recess into the tibia, said tool or tools being adapted to rotate about an axis which is parallel to but horizontally displaced from the longitudinal axis of the tibial alignment rod.

7. A set of instruments according to claim 6 in which said tool or tools includes a mandrel having an eccentric bore for engaging the protruding tibial alignment rod and having an outer cylindrical surface with a longitudinal axis parallel to but horizontally displaced from the axis of the tibial alignment rod, said tool or tools being arranged for rotation about the cylindrical surface of said mandrel.

8. A set of instruments according to claim 6 in which said tool or tools comprise a reamer for cutting out a surface of revolution in the proximal end of the tibia, and a broach for cutting an axial socket in the tibia.

9. A set of instruments according to claim 6 in which the tibial alignment rod is of a sufficient length to enable a first end thereof to be located within the tibial medulla adjacent the ankle joint whilst a second end thereof protrudes from the proximal end of the tibia.

10. A set of instruments according to claim 6 and including a tibial saw guide for cutting a tibial plateau on the proximal end of the tibia, the saw guide comprising means to slidably and rotatably accommodate the protruding tibial alignment rod, and a pair of slots to guide a saw to cut a complete tibia plateau on the proximal end of the tibia.

11. A set of instruments according to claim 10 in which the slots in the tibial saw guide are adjustable in position relative to the tibial alignment rod so as to allow the guide to be rotated about the whole of the tibia.

12. A set of instruments according to claim 6 and including a tibial impactor for pushing a tibial component of a knee prosthesis home within the axial socket, the impactor having an eccentric bore therein to accommodate the tibial alignment rod.

13. A set of instruments according to claim 1 and including an alignment rod introducer having means to grip an end of the alignment rod to allow the rod to be inserted into tibial or femoral medulla and thereafter to release the alignment rod when it is in the correct position in the medulla.

14. In a method of implanting a knee prosthesis, the steps of
    making an access hole in the femur between the femoral condyles; and
    inserting through said hole into the medulla of the femur a femoral alignment rod having a first blunt end and a second end opposite said first end until the first end is located within the medulla at least beyond the lesser trochanter with the second end protruding from the access hole such that the rod contacts the inner walls of the bone defining the medulla;
    while ensuring that the access hole is sufficiently larger than the diameter of the rod to impose no physical constraint thereon, whereby that portion of the rod which protrudes from the access hole extends linearly along an axis the position of which is dictated by points of contact within the medulla between the rod and the inner walls of the medulla.

15. In a method of implanting a knee prosthesis, the steps of making an access hole in the proximal end of the tibia, inserting one end of a tibial alignment rod in the tibial medulla as far as possible with the other end protruding from the end of the tibia, sliding one or more cutting tools over the protruding tibial alignment rod, and cutting a recess or recesses into the tibia which are centered on an axis which is parallel to but horizontally displaced from the longitudinal axis of the tibial alignment rod.

16. A femoral alignment rod for insertion within the medulla of a femur during surgical implantation of a knee prosthesis, the alignment rod being of intact integral unitary construction, and having a first blunt end for insertion within the medulla of the femur through an access hole located between the femoral condyles, and a second end opposite said first end, the length of the rod between said two ends being sufficient, with respect to the particular femur undergoing surgery, and the rod being sufficiently flexible, to allow said second end to protrude from said access hole whilst said first end is located within the medulla at least beyond the lesser trochanter, the rod also being resilient and the access hole being sufficiently larger than the diameter of the rod to impose no physical constraint thereon, such that once the rod is fully inserted within the medulla as aforesaid, the portion of the rod located within the medulla contacts the inner walls of the bone defining the medulla, whereby the portion of the rod which protrudes from the access hole is allowed to extend linearly along an axis the position of which is dictated by points of contact within the medulla between the rod and the inner walls of the medulla.

17. A femoral alignment rod for insertion within the medulla of a femur during surgical implantation of a knee prosthesis, the alignment rod having a first blunt end for insertion within the medulla of the femur through an access hole located between the femoral condyles, and a second end opposite said first end, the length of the rod between said two ends being sufficient, with respect to the particular femur undergoing surgery, and the rod being sufficiently flexible, to allow said second end to protrude from said access hole whilst said first end is located within the medulla at least beyond the lesser trochanter, the rod also being resilient and the access hole being sufficiently larger than the diameter of the rod to impose no physical constraint thereon, such that once the rod is fully inserted within the medulla as aforesaid, the portion of the rod located within the medulla contacts the inner walls of the bone defining the medulla, whereby the portion of the rod which protrudes from the access hole is allowed to extend linearly along an axis the position of which is dictated by points of contact within the medulla between the rod and the inner walls of the medulla, the rod further having an excavation adjacent said second end and within the confines of the profile of the rod for accommodating means releasably attachable thereat for thereby rotating, pulling and pushing the rod relative to the femur and its medulla.

* * * * *